US006345617B1

(12) United States Patent
Engelbreth et al.

(10) Patent No.: US 6,345,617 B1
(45) Date of Patent: Feb. 12, 2002

(54) AEROSOL MEDICATION DELIVERY APPARATUS AND SYSTEM

(75) Inventors: Dan Engelbreth; Robert Morton; Martin Foley, all of London; Mark Nagel, Mt. Brydges; Jolyon P. Mitchell, London, all of (CA)

(73) Assignee: 1263152 Ontario Inc., London (CA)

( * ) Notice: Subject to any disclaimer, the term of this patent is extended or adjusted under 35 U.S.C. 154(b) by 0 days.

(21) Appl. No.: 08/938,686

(22) Filed: Sep. 26, 1997

(51) Int. Cl.[7] ............................................. A61M 11/00
(52) U.S. Cl. ............................. 128/200.23; 128/200.18
(58) Field of Search ...................... 128/200.23, 200.18, 128/203.23, 203.18, 203.21, 200.14, 200.24, 205.24

(56) References Cited

U.S. PATENT DOCUMENTS

| 2,670,739 A | | 3/1954 | McNeill |
| 3,236,458 A | * | 2/1966 | Ramis .................. 128/200.18 |
| 3,556,122 A | | 1/1971 | Laerdal |

(List continued on next page.)

FOREIGN PATENT DOCUMENTS

| EP | 0 009 667 | 9/1979 |
| EP | 0 015 247 A1 | 1/1980 |
| EP | 0 134 847 | 8/1983 |

(List continued on next page.)

OTHER PUBLICATIONS

Anthony J. Hickey and Richard M. Evans "Aerosol Generation from Propellant–Driven Metered Dose Inhalers" pp. 417–435.

J.L. Rau, *Respiratory Care Pharmacology*, 4th ed. (1994, Mosby), pp. 256–261.

K. Meeran, A. Hattersley, J. Burrin, R. Shiner, K. Ibbertson, Oral and Inhaled Corticosteroids Reduce Bone Formation as Shown by Plasma Osteocalcin Levels, Am. J. Respir. Crit. Care Med 151:333–336.

S.P. Newman, *Aerosol Deposition Consideration in Inhalation Therapy*, Chest/88/2/Aug., 1985/[Supplement].

Merriam–Webster's Collegiate Dictionary, Tenth Ed., p. 86, ISBN 0–87779–707–2, 1997.*

*Primary Examiner*—John G. Weiss
*Assistant Examiner*—Teena Mitchell
(74) *Attorney, Agent, or Firm*—Brinks Hofer Gilson & Lione (57) ABSTRACT

An improved aerosol medication delivery apparatus and system. The aerosol medication delivery apparatus includes a canister-holding portion and a chamber housing. The canister-holding portion has a receptacle for receipt of a pMDI canister containing a medication and a propellant to provide the aerosol medication delivery system. The canister-holding portion has a discharge orifice communicating with the receptacle to direct an aerosol into an interior of the chamber housing at an input end thereof. The chamber housing also has an output end from which medication can be withdrawn by inhalation by a patient. According to one aspect, the aerosol delivery system includes a containment baffle located at the output end of the chamber housing to partially block the output. According to another aspect, the canister-holding portion and the chamber housing are coupled together by a mechanism that provides for the canister-holding portion to be retracted into the chamber housing for storage. The coupling mechanism also allows the canister-holding portion to be extracted from its storage position in the chamber housing and pivoted into position for use when dispensing medication. In another aspect, an aerosol medication apparatus includes a chamber housing with an input end to receive the discharge of a medication from a pMDI canister and an output end including a containment baffle that partially blocks the output end. The pMDI canister may be received in an elastomeric backpiece that is adapted to accommodate various sizes of actuator boot mouthpieces.

58 Claims, 6 Drawing Sheets

U.S. PATENT DOCUMENTS

| | | | |
|---|---|---|---|
| 3,565,071 A | | 2/1971 | Cobb et al. |
| 3,643,686 A | | 2/1972 | Koegel |
| 3,809,084 A | | 5/1974 | Hansen |
| 3,809,294 A | | 5/1974 | Torgeson |
| 3,838,686 A | | 10/1974 | Szekely |
| 3,897,779 A | | 8/1975 | Hansen |
| 3,994,421 A | | 11/1976 | Hansen |
| 4,174,712 A | | 11/1979 | Moren et al. |
| 4,292,966 A | | 10/1981 | Monö et al. |
| 4,470,412 A | | 9/1984 | Nowacki et al. |
| 4,509,515 A | * | 4/1985 | Altounyan et al. .... 128/200.23 |
| 4,637,528 A | | 1/1987 | Wachinski et al. |
| 4,641,644 A | * | 2/1987 | Andersson et al. .... 128/200.23 |
| 4,796,614 A | * | 1/1989 | Nowacki et al. ....... 128/200.14 |
| 4,846,168 A | | 7/1989 | Abiko et al. |
| 4,852,561 A | * | 8/1989 | Sperry ................... 128/200.23 |
| 4,907,583 A | * | 3/1990 | Wetterlin et al. ...... 128/200.18 |
| 4,940,051 A | | 7/1990 | Lankinen |
| 5,012,803 A | * | 5/1991 | Foley et al. ........... 128/200.23 |
| 5,012,804 A | | 5/1991 | Foley et al. |
| 5,033,463 A | * | 7/1991 | Cocozza ................ 128/203.15 |
| 5,040,527 A | | 8/1991 | Larson et al. |
| 5,042,467 A | | 8/1991 | Foley |
| 5,048,729 A | * | 9/1991 | Pritchard ............... 128/200.23 |
| 5,178,138 A | * | 1/1993 | Walstrom et al. ...... 128/200.23 |
| 5,241,954 A | | 9/1993 | Glenn |
| 5,250,287 A | | 10/1993 | Cocozza |
| 5,297,543 A | | 3/1994 | Larson et al. |
| 5,385,140 A | * | 1/1995 | Smith .................... 128/200.23 |
| 5,427,089 A | | 6/1995 | Kraemer |
| 5,477,849 A | | 12/1995 | Fry |
| 5,497,765 A | * | 3/1996 | Praud et al. ........... 128/200.23 |
| 5,505,194 A | | 4/1996 | Adjei et al. |
| 5,617,844 A | | 4/1997 | King |
| 5,676,130 A | * | 10/1997 | Gupte et al. ........... 128/200.18 |
| 5,724,959 A | * | 3/1998 | McAughey et al. ... 128/200.18 |
| 5,724,962 A | * | 3/1998 | Vidgren et al. ........ 128/205.24 |
| 5,738,087 A | | 4/1998 | King |
| 5,755,221 A | | 5/1998 | Bisgaard |
| 5,765,553 A | | 6/1998 | Richards et al. |
| 5,775,320 A | | 7/1998 | Patton et al. |
| 5,816,240 A | | 10/1998 | Komesaroff |
| 5,840,279 A | | 11/1998 | Narodylo et al. |
| 5,881,718 A | | 3/1999 | Mortensen et al. |
| 6,026,807 A | | 2/2000 | Puderbaugh et al. |
| 6,039,042 A | | 3/2000 | Sladek |
| 6,123,075 A | | 9/2000 | Kirk |
| 6,138,673 A | | 10/2000 | Shepherd |

FOREIGN PATENT DOCUMENTS

| | | |
|---|---|---|
| EP | 0 289 563 B1 | 5/1991 |
| EP | 0 514 085 A1 | 11/1992 |
| EP | 0 347 779 B1 | 5/1994 |
| EP | 0 475 257 B1 | 6/1994 |
| EP | 0 548 152 B1 | 7/1996 |
| EP | 0 514 085 B1 | 7/1997 |
| EP | 0 820 780 A1 | 1/1998 |
| EP | 0 585 379 B1 | 9/1998 |
| GB | 975754 | 5/1961 |
| GB | 1017032 | 12/1963 |
| GB | 2 000 555 A | 1/1979 |
| GB | 2 299 512 | 9/1996 |
| WO | WO 91/00117 | 1/1991 |
| WO | WO 96/32149 | 10/1996 |
| WO | WO 97/01365 | 1/1997 |
| WO | WO 97/31668 | 9/1997 |
| WO | WO 98/26827 | 6/1998 |
| WO | WO 99/16490 | 4/1999 |

* cited by examiner

AEROSOL MEDICATION DELIVERY APPARATUS AND SYSTEM

FIELD OF THE INVENTION

This invention relates to a portable aerosol medication delivery apparatus and system for administering a desired respirable dosage of a medication in aerosol form to a patient's lungs by oral inhalation.

BACKGROUND OF THE INVENTION

The use of aerosol medication delivery systems to administer medication in aerosol form to a patient's lungs by inhalation is well known in the art.

Conventional aerosol medication delivery systems include pressurized metered-dose inhalers (pMDIs). Conventional pMDIs typically have two components: a canister component in which the medication particles are stored under pressure in a suspension or solution form and a receptacle component used to hold and actuate the canister. The canister component typically includes a valved outlet from which the contents of the canister can be discharged. Aerosol medication is dispensed from the pMDI by applying a force on the canister component to push it into the receptacle component thereby opening the valved outlet and causing the medication particles to be conveyed from the valved outlet through the receptacle component and discharged from an outlet of the receptacle component. Upon discharge from the canister, the medication particles are "atomized" forming an aerosol. It is intended that the patient coordinate the discharge of aerosolized medication with his or her inhalation so that the medication particles are entrained in the patient's inspiratory flow and conveyed to the lungs. Typically, pMDIs have used propellants, such as chlorofluorocarbons (CFCs), to pressurize the contents of the canister and to propel the medication particles out of the outlet of the receptacle component Although conventional pMDIs have been widely used to provide many patients with the benefits of aerosol medication, conventional pMDIs have certain drawbacks. For example, an objective of aerosol therapy has been the optimization of the mass percentage of the respirable dose of an aerosol medication in order to optimize deposition in a patient's lungs to achieve a full therapeutic effect with the least possible side-effects. Conventional pMDIs may not have always been able to meet this objective.

One drawback associated with conventional pMDIs relates to the discharge velocity of the aerosol particles. Medication particles are stored under considerable pressure in the pMDI canister and as a consequence, their velocity may be high upon discharge.

Among other things, the effect of high velocity contributes to a significant number of aerosol medication particles impacting and depositing in the patient's oropharynx and upper airway rather than continuing their pathway through the upper airway and into the lungs. Such impaction and deposition may result in a significant portion of the medication dose being systemically absorbed or ingested. As documented in the literature [J. L. Rau, "Respiratory Care Pharmacology", $4^{th}$ ed. (1994, Mosby) at pp. 256–261; K. Meeran, A. Hattersley, J. Burrin, R. Shiner, K. Ibbertson K., "Oral and Inhaled Corticosteroids Reduce Bone Formation as Shown by Plasma Osteocalcin Levels", Am. J. Respir. Crit. Care Med 151:333–336], systemic absorption or ingestion of aerosol medication may cause a patient adverse side-effects, particularly when the aerosol medication is a corticosteroid. Some of these adverse side-effects include pharyngeal candidiasis, hoarseness, and adrenal suppression.

The high velocity of the aerosol medication particles may also accentuate the difficulty of a significant number of patients, particularly the very young and elderly, to coordinate actuation of the pMDI with inhalation of the aerosol medication particles generated. Failure to coordinate the actuation and inhalation maneuvers and failure to inhale slowly, have been documented by the literature [S. P. Newman, "Aerosol Deposition Considerations in Inhalation Therapy" Chest/88/2/August, 1985/Supplement] as contributing to a significant reduction in the number of aerosol medication particles inspired and deposited in a patient's lungs.

Impaction and deposition of aerosol medication particles on a patient's oropharynx and upper airway may also contribute to an unpleasant taste in a patient's mouth, particularly with certain medication solution or suspension formulations such as flunisolide.

In addition to high particle velocity, a significant number of large non-respirable medication particles may be produced upon discharge as a result of the medication suspension or solution formulation as well as the atomization process. As mentioned above, conventional pMDIs have used CFCs to propel the medication out of the pMDI actuator outlet. In view of environmental concerns with CFCs, there has been a growing interest in using non-CFC propellants, such as hydrofluoroalkanes (HFAs).

Accordingly, it is an object of the invention to provide for the delivery of respirable medication particles from a pMDI canister with a device that overcomes the disadvantages of the prior art.

It is another object to provide a device which reduces the need for a patient to coordinate activation of a pMDI canister with inhalation.

It is a further object to provide a device that reduces the delivery of non-respirable medication particles from a pMDI canister to a patient.

It is yet another object to provide a device that reduces the impaction of medication particles on a patient's oropharynx and upper airway.

It is still another object to provide a device for the delivery of aerosol medication from a pMDI canister that uses an HFA propellant instead of a CFC propellant.

SUMMARY OF THE INVENTION

In order to address the above noted objectives, as well as other objectives, the present invention provides an improved aerosol medication delivery apparatus. The aerosol medication delivery apparatus includes a canister-holding portion and a chamber housing. The canister-holding portion has a receptacle for receipt of a pMDI canister containing a medication and a propellant. The canister-holding portion has a discharge orifice communicating with the receptacle to direct an aerosol into an interior of the chamber housing at an input end thereof. The chamber housing also has an output end from which medication can be withdrawn by inhalation by a patient. The canister-holding portion and the chamber housing are coupled together by a mechanism that provides for the canister-holding portion to be retracted into the chamber housing for storage. The coupling mechanism also allows the canister-holding portion to be extracted from its storage position in the chamber housing and pivoted into position for use when dispensing medication. According to one aspect of the present invention, the aerosol delivery system includes a containment baffle located at the output end of the chamber housing to partially block the output end.

According to another aspect, the canister-holding portion and the chamber housing are coupled together by a mechanism that provides for the canister-holding portion to be retracted into the chamber housing for storage. The coupling mechanism also allows the canister-holding portion to be extracted from its storage position in the chamber housing and pivoted into position for use when dispensing medication.

In another aspect, an aerosol medication delivery apparatus includes a chamber housing with an input end an output end. The input end receives the discharge of a medication from a pMDI canister and the output end includes a containment baffle that partially blocks the output end. The pMDI canister is received in an elastomeric backpiece that is adapted to accommodate various sizes of actuator boot mouthpieces.

DETAILED DESCRIPTION OF THE PRESENTLY PREFERRED EMBODIMENTS

I. General

FIGS. 1–11 show an embodiment of an aerosol medication delivery apparatus 10. The apparatus 10 comprises a pMDI canister-holding portion (or dispenser) 22 coupled to a chamber housing portion 24. The delivery apparatus 10 together with a pMDI canister 30 form an aerosol therapy system 12.

Figure 1:
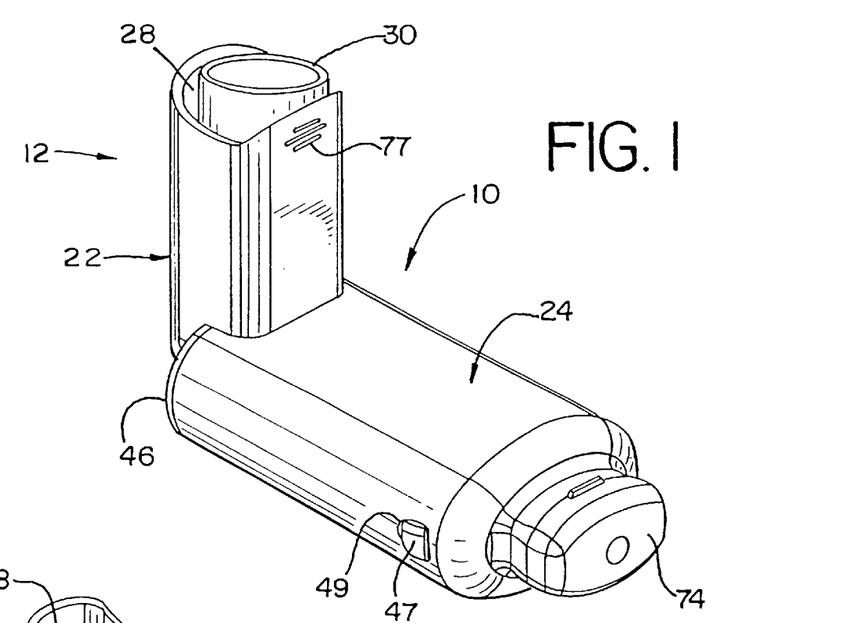
FIG. 1 is a perspective view of an aerosol medication delivery system in accordance with an embodiment of the present invention.

The canister-holding portion 22 has a generally rectangular cross-sectional shape that defines a receiving area or receptacle 28 for receipt therein of the pMDI canister 30. The receiving area 28 is suited for conventional pMDI canisters of well-known construction. The pMDI canister 30 contains a medication suspension or solution under pressure. In the present embodiment, an HFA propelled medication suspension or solution formulation is used. In one embodiment, the liquid medication is flunisolide. Other propellants and other medications may also be used.

Figure 6:
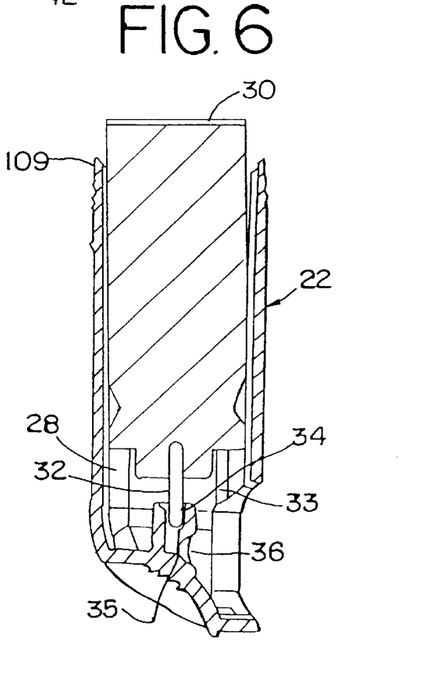
FIG. 6 is a sectional view of the canister-holding portion of FIG. 5 taken along line 6–6'.

Referring to FIG. 6, the pMDI canister 30 has a stem 32 that permits a portion of the medication suspension or solution to be discharged therefrom upon application of a force on the stem 32. When the pMDI canister 30 is located in the receiving area 28 of the canister-holding portion 22, the canister stem 32 is positioned in a vertical channel or well 34 formed in the bottom of the canister-holding portion 22. When the stem 32 of the canister 30 is located in the vertical channel 34, ambient air can pass into the chamber via a passageway 33. A horizontal passage 35 communicates with the vertical channel 34. The horizontal passage 35 leads to a discharge orifice 36 located opposite from the vertical channel 34.

II. Chamber Housing

Referring to FIG. 6, the discharge orifice 36 forms the passage by which medication particles from the pMDI canister 30 can exit the canister holding portion 22 and enter into the chamber housing portion 24. The chamber housing 24 has an input end 46 and an output end 48 that define the ends of an interior space 39.

Figure 2:
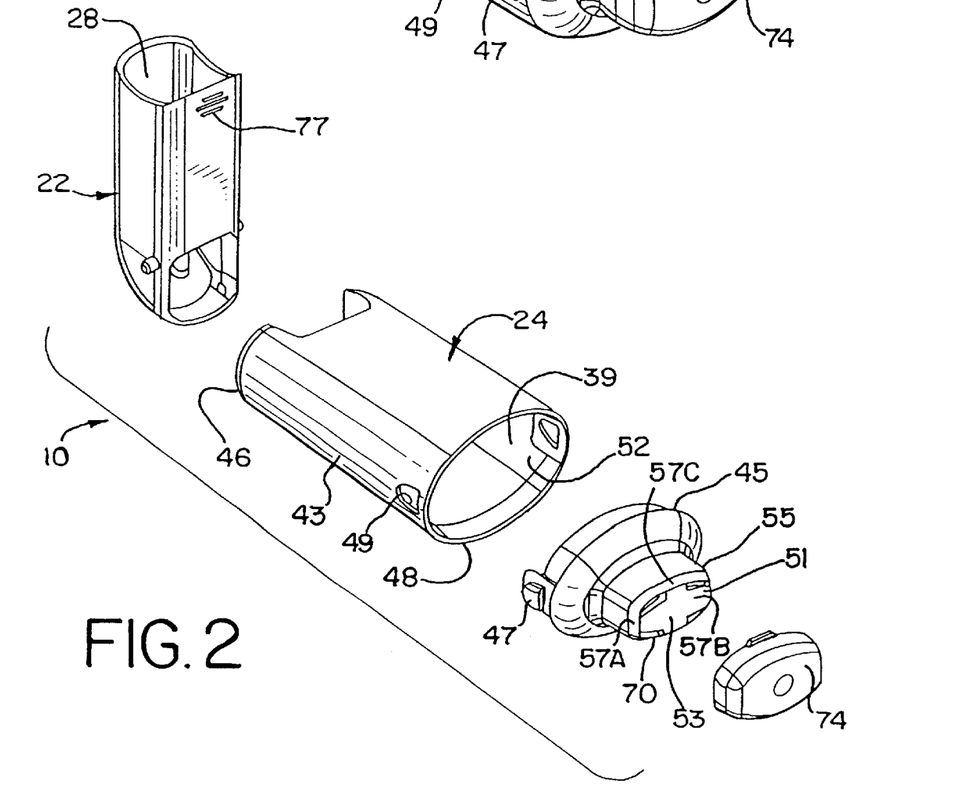
FIG. 2 is an exploded view of the aerosol medication delivery system of FIG. 1.
Figures 3, 4:
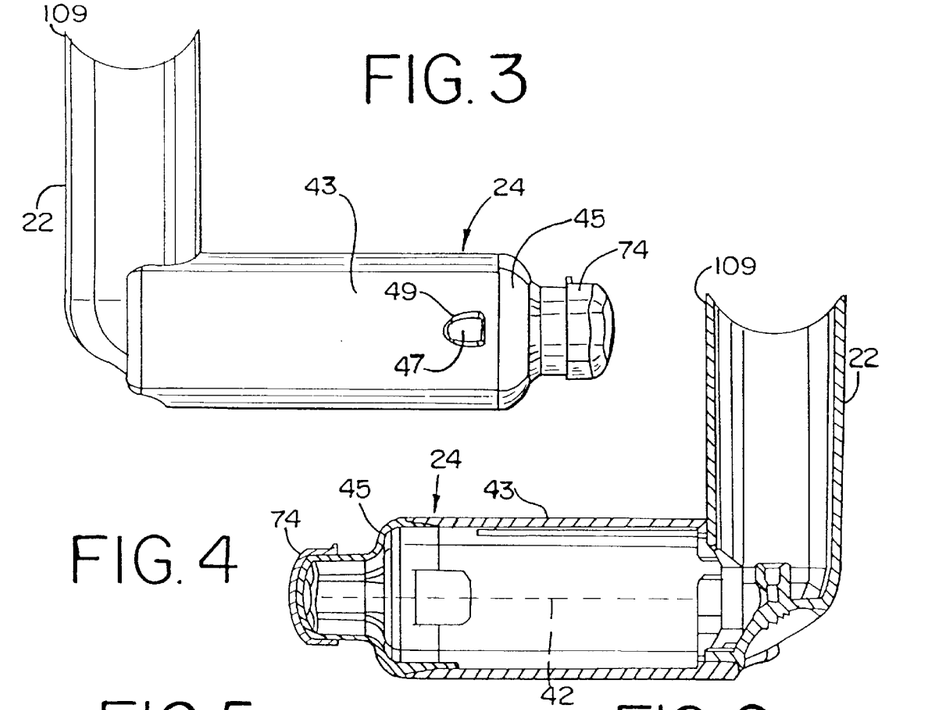
FIG. 3 is a side view of the aerosol medication delivery system of FIG. 1.
FIG. 4 is a side sectional view of the aerosol medication delivery system of FIG. 1.

Referring to FIGS. 2–4, in a present embodiment, the chamber housing portion 24 is formed of two parts: a main housing portion 43 and a downstream portion 45. The main housing portion 43 and the downstream portion 45 together define the interior space 39 of the chamber housing portion 24. The downstream portion 45 has retaining fingers 47 that engage in slots 49 on each side of the main housing portion 43. In the embodiment shown, the main housing portion 43 and the downstream portion 45 easily snap together and can be easily disconnected for cleaning.

Referring to FIG. 2, the main housing portion 43 has a curved cross section. In a present embodiment, the curved cross-section has a complex geometry formed of a plurality of radii to form a convenient, easy-to-use shape.

III. Containment Baffle/Mouthpiece

Figure 7:
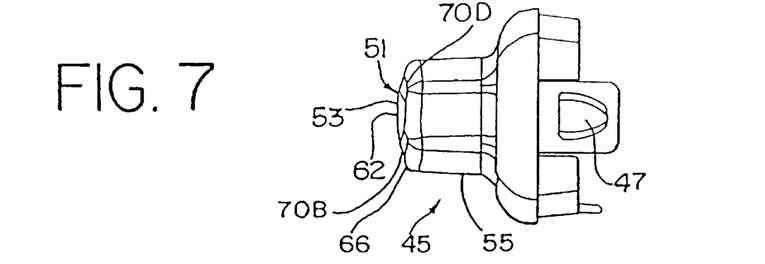
FIG. 7 is a side view of the downstream housing portion in FIG. 1.
Figure 8:
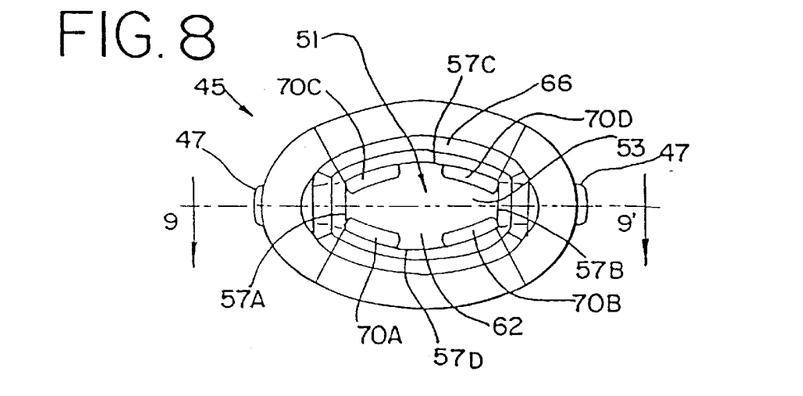
FIG. 8 is an end view of the downstream housing portion shown in FIG. 7.
Figure 9:
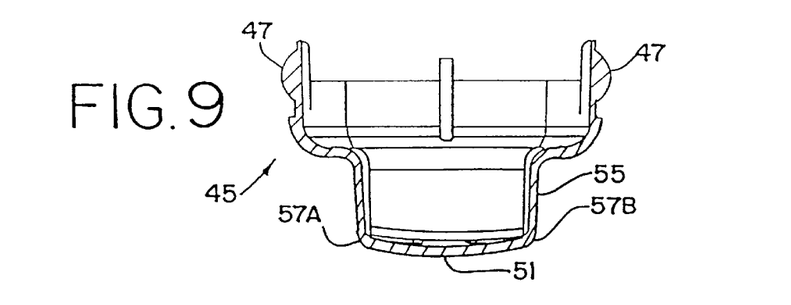
FIG. 9 is a sectional view of the downstream housing portion shown in FIG. 8 taken along line 9–9'.

Referring to FIGS. 2 and 7–9, a containment baffle 51 is located in the downstream portion 45 at the outlet of the chamber housing 24. The containment baffle 51 is located centrally and forms a distal wall 53 of the downstream portion 45. The containment baffle 51 is positioned so as to partially block the output end 48. The containment baffle 51 reduces the velocity or flow rate or both of the aerosol medication particles on axis 42 of the chamber housing 24. A mouthpiece 55 is located on the outside of the downstream portion 45 and includes the containment baffle 51 at an outlet end thereof As shown in FIGS. 7–9, the containment baffle 51 has a concave-shaped center portion 62. In the embodiment shown, the perimeter of the concave-shaped center portion 62 of the containment baffle 51 has generally straight vertical sides 57A and 57B, a curved top side 57C. and a curved bottom side 57D. The perimeter of the concave-shaped center portion 62 of the containment baffle 51 conforms generally in shape to the cross-sectional shape of the mouthpiece 55. The concave-shaped center portion 62 of the containment baffle 51 is aligned with a central axis 42 of the chamber housing 24 and is directly in line with the discharge orifice 36. Aerosol medication particles that have a flow path away from the axis of symmetry 42 tend to have a velocity that is lower than that of particles near to the axis of symmetry. The center portion 62 of the containment baffle 51 reduces the forward, on-axis velocity and simultaneously acts as an impaction surface for on-axis projectile aerosol medication particles. At the same time the center portion 62 allows slower moving aerosol medication particles to migrate towards the sides 52 of the chamber housing 24. The forward velocity of the aerosol medication particles away from the axis 42 along the chamber length is also reduced by the outer portion 66 of the containment baffle 51 that is concentric with the concave shaped center portion 62.

Positioned between the center and outer portions 62 and 66 is an inhalation opening area 70. In the embodiment, the inhalation opening area 70 is defined by four openings 70A–70D. The openings are arcuate in shape and conform to the periphery of the central portion 62. Each of the openings 70 has a length of approximately 9 mm and a width of approximately 2 mm. The size, shape and number of openings may vary depending on the medication suspension or solution formulation and/or propellant used.

In a present embodiment, the aerosol delivery apparatus 10 includes a cap 74 which can be placed over the mouthpiece 55 to prevent contaminants from entering the interior space 39. The cap 74 serves to protect the mouthpiece 55 and keep it relatively clean.

IV. Operation

To use the aerosol delivery apparatus 10 for delivery of an aerosol medication, the canister-holding portion 22 and chamber housing 24 are arranged as shown in FIG. 1. The cap 74 is removed and the pMDI canister 30 is located in the receiving area 28 with the stem 32 inserted into the channel 34 formed in the bottom of the receiving area 28 as shown in FIG. 6. As mentioned above, the apparatus 10 receives the pMDI canister 30 which is operated conventionally (i.e. by pressing down on the pMDI canister 30 which is located stem-side-down in the receiving area 28). Upon depression of the stem 32, the medication suspension or solution formulation in the pMDI canister 30 is discharged out of an opening 33 at the tip of the stem 32. As the medication suspension or solution formulation flows through the horizontal channel 35 and out of the discharge orifice 36, the propellant and suspending liquid or solvent evaporate and the medication particles are discharged in aerosol form into the surrounding environment inside the chamber volume 39. Upon discharge from the pMDI canister 30, the medication particles in the aerosol plume may have an average speed, size distribution and/or flow rate that may not be ideal for direct inhalation by a patient. However, once the aerosol medication is inside the chamber volume 39, the proportion of larger non-respirable particles available on inhalation is minimized and the dose of respirable particles is optimized. The aerosol medication particles are withdrawn therefrom by having the patient, whose mouth is around the mouthpiece 55, inhale through the inhalation opening area 70. The aerosol medication particles will then flow through the inhalation opening area 70 and into the patient's mouth.

V. Retraction for Storage

Figure 10:
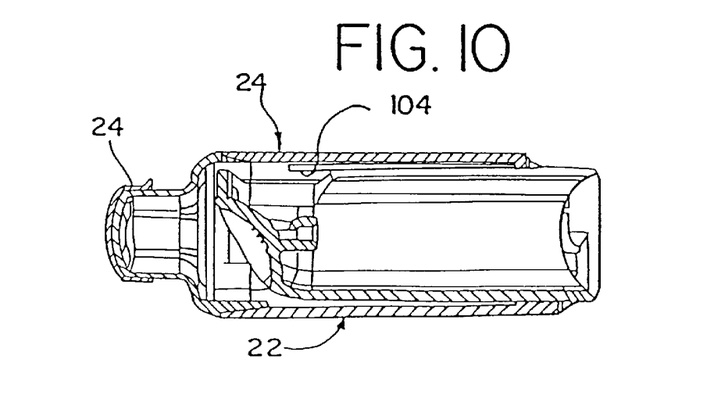
FIG. 10 is a sectional view of the embodiment in FIG. 1 in a retracted position.
Figures 11, 12:
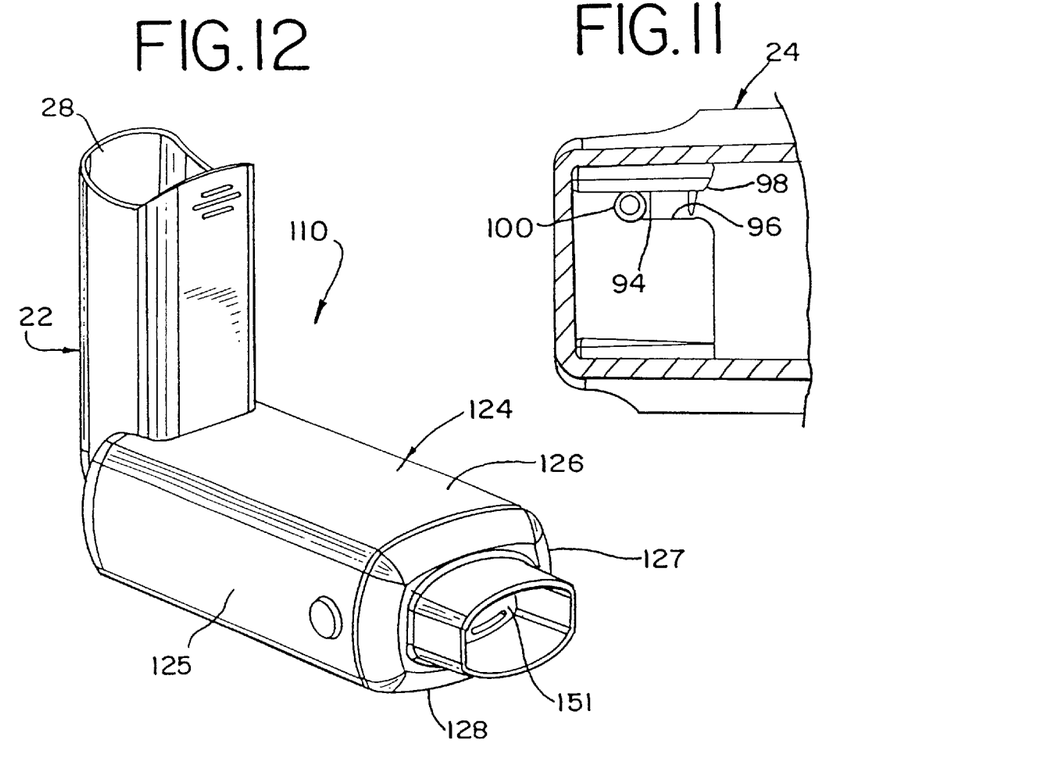
FIG. 11 is an enlarged sectional view of an inside upstream portion of the chamber housing of FIG. 1 showing part of the coupling mechanism.
FIG. 12 is a perspective view of an aerosol medication delivery system in accordance with another embodiment of the present invention.

A further feature of the aerosol medication apparatus 10 is that it can be retracted for convenient storage and portability. For this purpose, the chamber housing 24 is coupled to the canister-holding portion 22 via a coupling mechanism 94 as shown in FIG. 11. The coupling mechanism 94 permits the aerosol medication delivery apparatus 10 to be compactly stored by pivoting the canister-holding portion 22 from the position of FIGS. 1–4 to a horizontal position and then pushing the canister-holding portion 22 so that it translationally moves into the chamber housing 24 as shown in FIG. 10.

Figure 5:
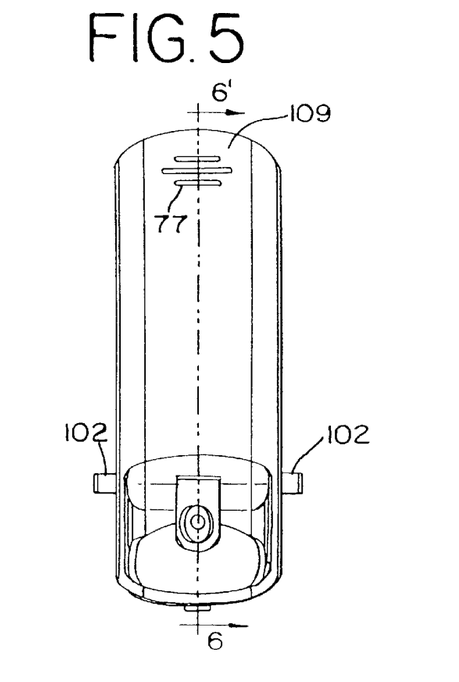
FIG. 5 is a front view of the canister-holding portion shown in FIG. 1.

Referring to FIG. 11, the pivoting and translational movement is accomplished by the structure of the coupling mechanism 94. In particular, the coupling mechanism 94 includes a pair of slots 96 formed in the chamber housing 24, wherein each slot 96 has an open end 98 and a closed end 100. As shown in FIG. 5, the canister-holding, portion 22 has a pair of pegs 102, attached thereto. In addition, the interior portion of the chamber housing 24 has multiple parallel tracks 104 (shown in FIG. 10) which guide the canister-holding portion 22 into the chamber housing 24.

To connect the chamber housing 24 and the canister-holding portion 22 together, a top end 109 of the canister-holding portion 22 is first inserted into the output end 48 of the chamber housing 24 and translationally moved towards and past the input end 46 so that the pegs 102 are inserted into the open ends 98 of the corresponding slots 96. Each of the pegs 102 can then translationally move within its respective slot 96 to the closed end 100 thereof. Thus, the canister-holding portion 22 is telescopically received within the chamber housing 24 during translational movement and is able to move from the retracted position of FIG. 10 to an extended position. At the extended position, both pegs 102 contact the closed ends 100 of their corresponding slots 96 and the canister-holding portion 22 is then allowed to pivot to the position of FIG. 4 so that the patient can use the apparatus 10. The end of the canister-holding portion 22 is curved so as to allow it to pivot relative to the chamber housing 24. The foregoing coupling and retraction mechanism allow for easy use, transport, and lower manufacturing costs.

To facilitate handling by the patient, a plurality of ribs 77 may be located along the front and rear sides of the canister-holding portion 22 close to the top edge 109 thereof. These ribs 77 remain exposed when the canister-holding portion 22 is retracted into the chamber portion 24 so that the patient can use these ribs to help grip the end of the canister-holding portion 22 in order to withdraw it from the chamber portion 24. After use by the patient, the cap 74 can be placed back over the mouthpiece 55.

VI. Advantages of Disclosed Embodiment

With the embodiment disclosed above, the end result of combining the specified inhalation opening area 70, the chamber housing 24, and the containment baffle 51 is to administer a controllable and desired respirable dose of aerosol medication to a patient for inhalation into the lungs. Further, the disclosed embodiment provides advantages over prior devices in that it incorporates an integrated actuator and is easier to use and is easier to store and carry given its smaller size.

An advantageous feature of the disclosed embodiment is provided by the containment baffle 51. As mentioned above, the velocity of the aerosol medication particles nearest the axis of symmetry 42 will typically be greater than that of aerosol medication particles that are located further from the axis 42. The velocity of the aerosol medication particles near the axis 42 may be so large as to reduce the effectiveness of delivering the medication to the patient because it will cause a significant portion of the aerosol medication particles to impact on the oropharyngeal region and upper airway where they have no therapeutic value and, in the case of medication such as corticosteroids, may give rise to adverse side-effects. The containment baffle 51 overcomes this potential problem by isolating the patient's mouth from the location at which the greatest risk of high velocity impaction may occur. The containment baffle provides this solution in a manner that is relatively inexpensive and easy to manufacture.

The disclosed aerosol medication delivery apparatus optimizes the deposition of respirable aerosol medication particles in a patient's lungs to provide a desired therapeutic effect. The aerosol medication delivery apparatus also reduces the importance of coordination between the actuation and inhalation maneuvers and reduces or eliminates possible side-effects caused by aerosol medication formulations consisting of corticosteroids. The aerosol medication delivery apparatus also reduces or eliminates the unpleasant taste associated with aerosol medication formulations such as flunisolide and allows for convenient portability and quick use.

In the case of pMDIs that use HFA as a propellant for flunisolide, the present embodiment provides a particular advantage. Through use of the present embodiment, the respirable dosage of flunisolide delivered to the patient can be controlled in a manner to closely conform to the dosage of flunisolide that had been delivered using conventional prior art systems that used prior propellants, such as CFC. In this manner, the dosage of flunisolide can be consistently maintained, thereby benefiting administration of such medication to patients.

The shape, size, and number of openings in the inhalation opening area may vary in order to ensure the administration of a desired respirable dose of a specific pMDI formulation. Upon discharge the on-axis aerosol medication particles, which are generally non-respirable and have a higher inertia than the respirable particles, collide with the interior center portion of the containment baffle resulting in a reduction in the number of larger (non-respirable) aerosol medication particles, and the division of larger (non-respirable) aerosol medication particles into smaller respirable particles.

By sealing off (except for the inhalation opening area) the output end of the chamber, the containment baffle contributes to maintaining a high pressure zone in the chamber which allows for the deflection of most slower moving respirable aerosol medication particles away from the containment baffle and into the chamber for containment until inhaled by the patient through the inhalation opening area. The containment of the respirable aerosol medication particles in the chamber provides the patient with more time to inhale the aerosol medication particles and, therefore, reduces the importance of exact coordination between the discharge maneuver and inhalation.

VII. Exemplary Embodiment

In one exemplary embodiment, shown in FIGS. 1–11, the canister-holding portion 22 is approximately 7.5 cm in height and is approximately 2.5 by 2.5 cm in cross section. The chamber housing 24 is approximately 8 cm in length and has an oval-shaped cross section with dimensions of approximately 49 mm by 33 mm. The mouthpiece 55 is approximately 1.5 cm in length. The canister-holding portion, the chamber housing, and the end cap are formed of a suitable hard, durable plastic, such as polypropylene. The discharge orifice 36 has a diameter of approximately 0.011 inches. In a present embodiment, the containment baffle 51 has a width of approximately 27 mm and a height of approximately 15 mm at the center and 5 mm at the side edges.

For purposes of this embodiment, it is assumed that the pMDI canister contains a 0.06% w/v to 0.24% w/v mixture of liquid medication, such as flunisolide in ethanolic solution and HFA as a propellant. It is understood that the pMDI canister 30 can also contain other liquids and other mixtures without departing from the spirit of the invention.

VIII. Alternative Embodiments

Figure 13:
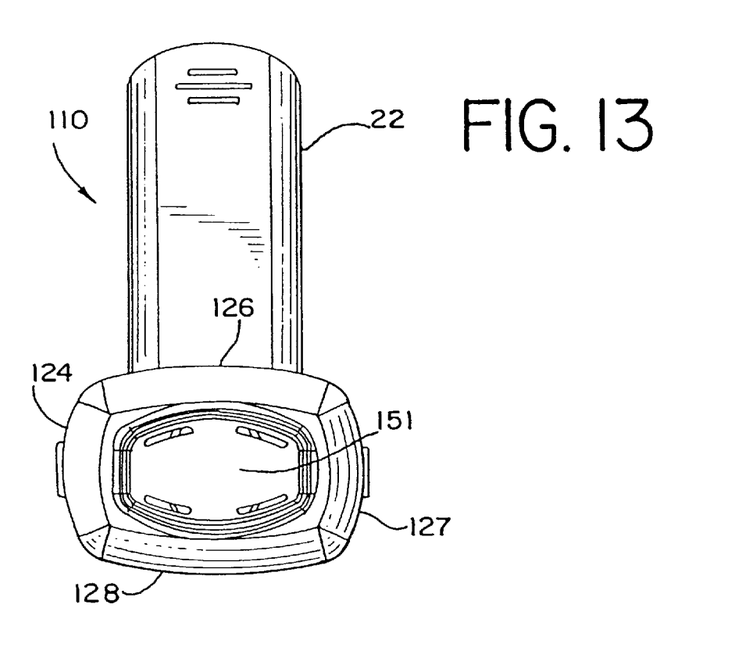
FIG. 13 is an end view of the embodiment of FIG. 12.

Referring to FIGS. 12 and 13, another embodiment of an aerosol delivery apparatus 110 is shown. This embodiment is similar to the embodiment shown in FIGS. 1–11 and like components are labeled with the same numerals. In the embodiment of FIGS. 12 and 13, the containment baffle 151 is located at an upstream end of the passageway defined in the mouthpiece 55. The containment baffle 151 in this embodiment is convex in shape and diverts flow around an on-axis trajectory. In the embodiment of FIGS. 12 and 13, a chamber housing 124 has four squared-off sides 125, 126, 127, and 128. The squared-off sides may facilitate gripping of the device.

Figures 14, 15, 16, 17, 18:
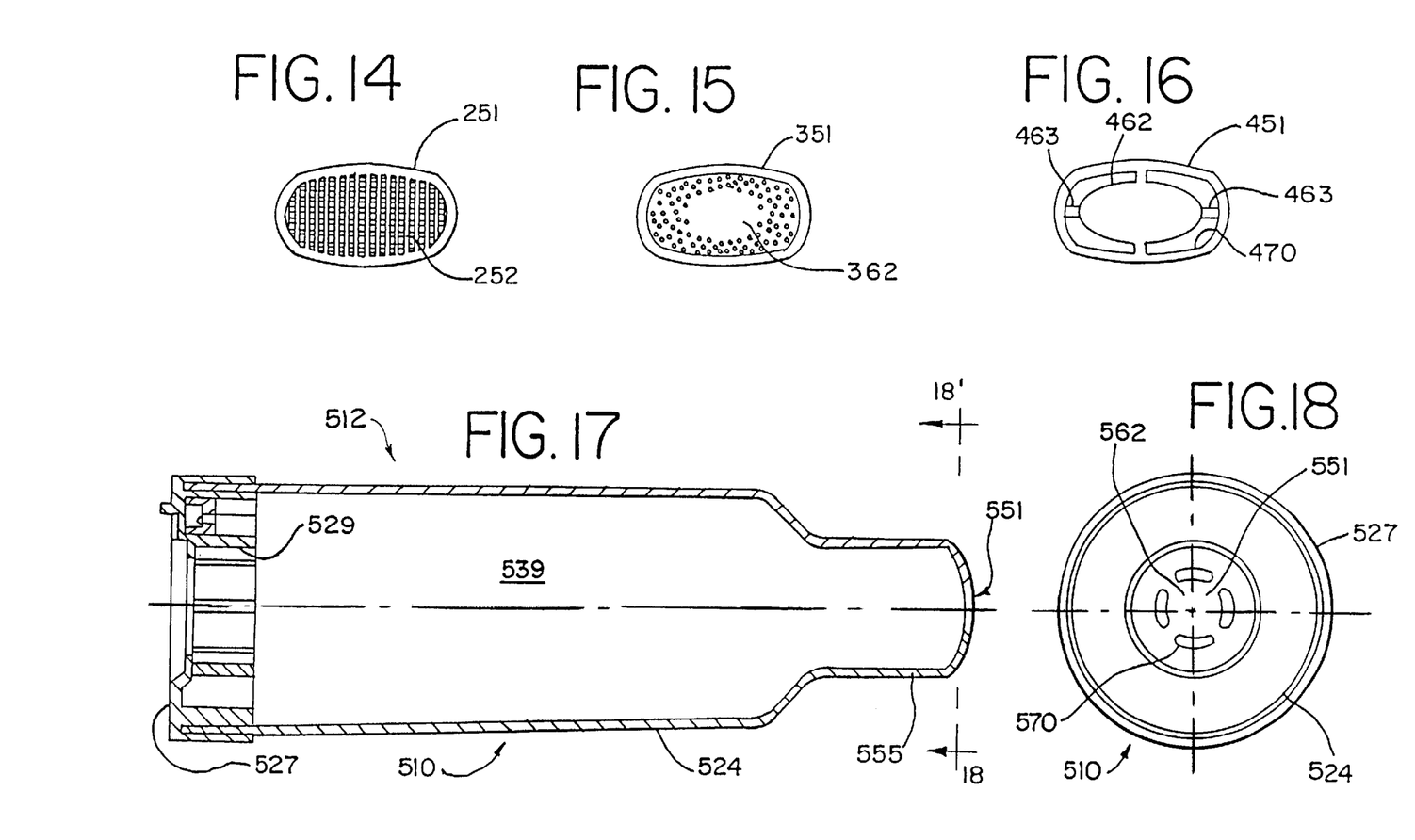
FIGS. 14–16 each show an end view of an alternative embodiment of the containment baffle shown in FIG. 8.
FIG. 17 is a side sectional view of another alternative embodiment of the aerosol medication delivery apparatus of FIG. 1.
FIG. 18 is a end view of the embodiment shown in FIG. 17

Referring to FIGS. 14–16, there are depicted alternative embodiments of the containment baffle. In FIG. 14, a containment baffle 251 has a screen-like structure forming a plurality of openings defined between a crisscrossed mesh 252. The surface area provided by the mesh 252, combined with the relatively small areas of the openings, serves to prevent aerosol particles having a high velocity from passing to the patient. In FIG. 15, a containment baffle 351 has a plurality of small circular openings formed around a periphery of a solid central portion 362. Like the previous embodiments, the embodiment of FIG. 15 provides a surface area 362, combined with the relatively small openings, serves to prevent aerosol particles having a high velocity from passing to the patient. In FIG. 16, a containment baffle 451 has four relatively large openings formed around the periphery a solid dish-shaped central portion 462. The dish-shaped central portion 462 is connected to the remainder of the chamber body by one or more ribs 463. Like the previous embodiments, the embodiment of FIG. 16 provides a surface area 462, that serves to prevent aerosol particles having a high velocity from passing to the patient.

Referring to FIGS. 17 and 18, there is shown an alternate embodiment 512 of an aerosol delivery apparatus. The embodiment of FIGS. 17 and 18 includes an aerosol delivery apparatus 510. The apparatus 510 includes a chamber housing 524 which defines an interior space 539. The apparatus 510 does not include an integrated canister-holding portion. Instead, the chamber housing 524 has a backpiece 527. The backpiece 527 is made of an elastomeric material and is fitted over the upstream end of the chamber housing 524. The backpiece 527 has an opening 529 located centrally therein. The opening 529 is sized to receive the mouthpiece end of a separate pMDI actuator boot. In a preferred embodiment, the opening 529 is sized so that the mouthpiece of the pMDI actuator boot fits snugly into the opening 529. Because the backpiece 527 is formed of an elastomeric material, it is resilient and the opening 529 in the backpiece can be stretched, thereby enabling it accommodate actuator boot mouthpieces of various sizes and shapes. The backpiece 527 may be similar to the backpiece described in U.S. Pat. No. 4,470,412 or in Ser. No. 08/248,716, the entire disclosure of which is incorporated by reference herein.

Located at a downstream end of the chamber housing 524 is a mouthpiece 555. Also located at the downstream end of the chamber housing 524 is a containment baffle 551. The containment baffle 551 may be similar to the containment baffle 51 in the above described embodiment. Located around the periphery of the containment baffle center portion 562 is an inhalation opening area 570. The inhalation opening area 570 includes four arcuate shaped openings. In the embodiment of FIGS. 17 and 18, the containment baffle 551 is located at the downstream end of the mouthpiece 555, although in alternative embodiments, the containment baffle may be located at the upstream end of the mouthpiece or anywhere along the length of the mouthpiece.

With the embodiment of FIGS. 17 and 18, the patient inserts the actuator boot mouthpiece into the opening 529 and inserts the pMDI canister into the actuator boot. The patient presses down on the pMDI canister to cause a plume of aerosol medication to be discharged from the stem of the pMDI canister out of the mouthpiece of the actuator boot and into the interior space 539. The patient inhales the aerosol from the interior space 539 via the mouthpiece 555 of the apparatus 510.

Figures 19, 20:
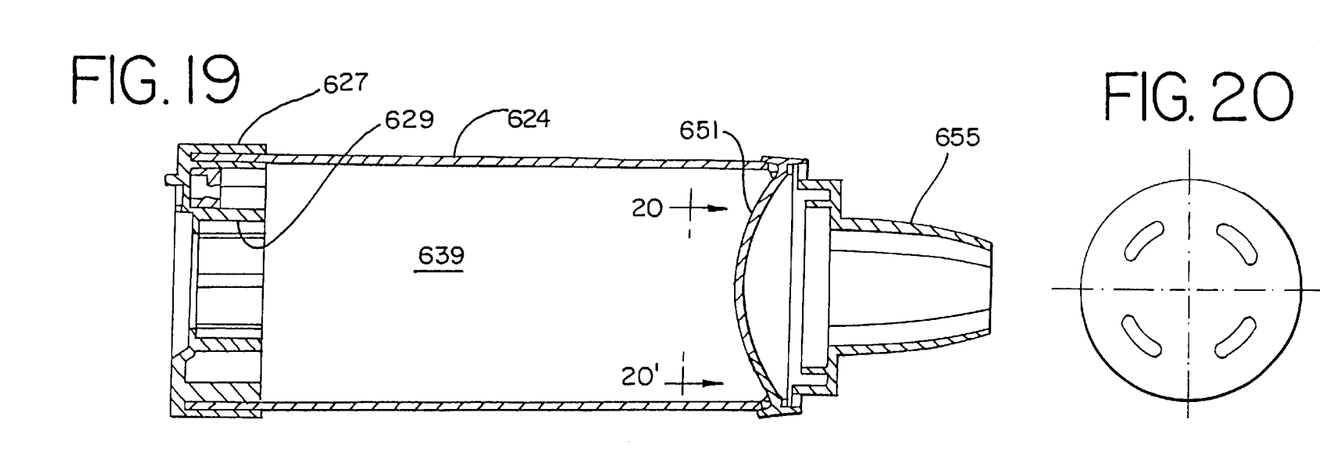
FIG. 19 is a side sectional view of yet another alternative embodiment of the aerosol medication delivery apparatus of FIG. 1.
FIG. 20 is an end view of the containment baffle of the embodiment of FIG. 19.

Another embodiment of the aerosol medication delivery apparatus is shown in FIGS. 19 and 20. An aerosol delivery apparatus 610 includes a chamber housing 624 defining an interior space 639. The apparatus 610 also includes an elastomeric backpiece 627 which may be similar to the backpiece in the embodiment shown in FIGS. 17 and 18. The apparatus 610 includes a containment baffle 651. The containment baffle 651 is located at the downstream end of the chamber housing 624 just upstream of the mouthpiece 655. The containment baffle 651 includes an inhalation opening area 670 located around the periphery of the containment baffle 651. In the embodiment of FIGS. 19 and 20, the containment baffle 651 may be formed of a single piece of material with the chamber housing 624. The mouthpiece 655 may be formed of a separate piece of material that is coupled to the downstream end of the chamber housing 624. The embodiment of FIGS. 19 and 20 may be used in a similar manner as the embodiment of FIGS. 17 and 18.

Figure 21:
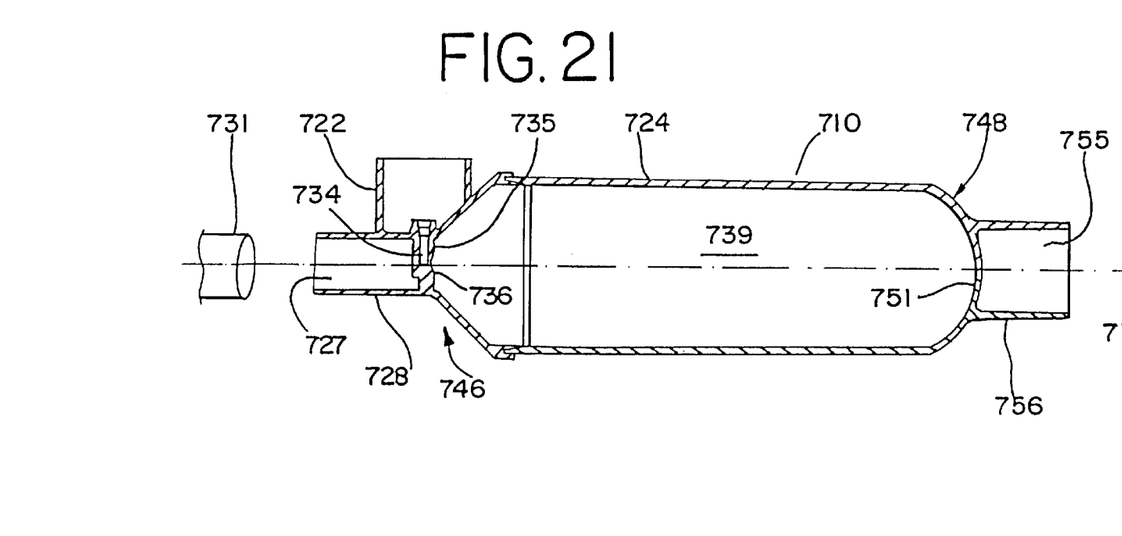
FIG. 21 is a side sectional view of yet another alternative embodiment of the aerosol medication delivery apparatus of FIG. 1.
Figure 22:
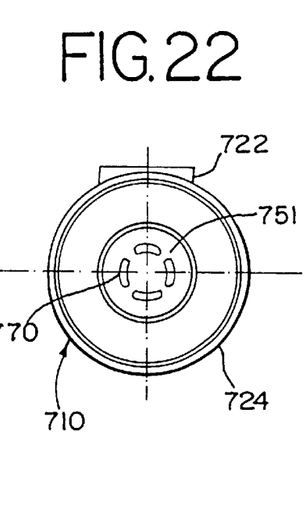
FIG. 22 is an end view of the containment baffle of the embodiment of FIG. 21.

Still another embodiment of the aerosol medication delivery apparatus is shown in FIGS. 21 and 22. This embodiment of the aerosol delivery apparatus is particularly suited for use by a mechanically ventilated patient (i.e. a patient using a ventilator). In FIG. 21, an aerosol delivery apparatus 710 includes components that are similar to the previous embodiments, in particular the embodiment of FIGS. 17 and 18. A chamber housing 724 defines an interior space 739. The apparatus 710 is intended to be positioned in a ventilator circuit, in particular in the air passageway that provides inspiratory air flow from a ventilator to the patient. The chamber housing 724 includes a first opening 727 located in a first tubular extension 728 extending from the upstream end 746 of the chamber housing 724 and a second opening 755 located in a second tubular extension 756 that extends from the downstream end 748 of the chamber housing 724. The first opening 727 connects to tubing 731 that leads to the ventilator (not shown) and the second opening 755 leads to tubing, a mask, a mouthpiece, or other suitable means (not shown) of providing air from the ventilator to the patient. Located at the upstream end of the chamber 724 is a receptacle 722. At the bottom of the receptacle 722 is a well 734 adapted to receive the stem of a pMDI canister. The well 734 extends into a rib 735 that extends across the entrance into the interior space 739 of the chamber housing 724. The rib 735 may be located at or along the extension 728. The rib 735 includes a discharge opening 736 that communicates with the well 734. The discharge opening 736 is oriented toward the interior space 739. The receptacle 722, the rib 735, and the discharge opening 736 are integrated with the chamber housing 724 forming part of the aerosol delivery apparatus 710, (i.e. the receptacle and chamber housing form an integrated unit). In one embodiment the receptacle 722, the rib 735, and the discharge opening 736 are formed of the same piece of material as the chamber housing 724, or alternatively, they may be formed of separate pieces. Further disclosure regarding an integrated chamber housing and canister receptacle is included in U.S. Pat. No. 5,012,804.

Located at the downstream end 748 of the chamber 724 is a containment baffle 751. The containment baffle 751 may be located at the downstream end of the chamber housing 724 or along the extension 756. The containment baffle 751 includes an inhalation opening area 770 located around the periphery of the containment baffle 751.

The embodiment of FIGS. 21 and 22 may be used in a similar manner as the device disclosed in U.S. Pat. No. 5,012,804. The apparatus 710 may be positioned in the inspiratory flow path from the ventilator to the patient when the patient is initially placed on the ventilator. The apparatus 710 is then left in place until needed. Alternatively, the apparatus 710 may be positioned in the inspiratory flow path of the ventilator circuit just prior to when a dose of aerosol medication is to be delivered to a ventilated patient. A pMDI canister is positioned in the receptacle 722 and actuated. The medication from the pMDI canister is conveyed with the inspiratory flow from the ventilator to the patient. As in the previously described embodiments, the containment baffle 751 reduces on-axis non-respirable particles.

The invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing descriptions.

We claim:

1. An aerosol medication delivery apparatus for use with a pressurized metered dose inhaler canister having medication and a propellant contained therein under pressure, where the pressurized metered dose inhaler canister has a discharge orifice from which the medication and the propellant can be discharged forming an aerosol, the apparatus comprising:

a chamber housing having an input end and an output end and defining an interior space, wherein said input end is adapted to receive a medication discharged from the discharge orifice of a pressurized metered dose inhaler canister into said interior space and said chamber housing having a central axis and a downstream end; and a containment baffle located at said downstream end of said chamber housing to partially block said output end, wherein said containment baffle has a curved portion located along and intersecting said central axis of said chamber housing, wherein said curved portion of said containment baffle remains fixed along said central axis relative to said output end of said chamber housing, and wherein said curved portion has a concave surface facing said input end of said chamber housing.

2. The invention of claim 1 further comprising a mouthpiece located at said output end of said chamber housing, wherein said mouthpiece forms said containment baffle.

3. The invention of claim 2 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

4. The invention of claim 2 further comprising a curved shoulder portion transitioning between said chamber housing and said mouthpiece.

5. The invention of claim 4 wherein an inner surface of said curved shoulder portion is concave.

6. The invention of claim 2 wherein said containment baffle is located at a downstream end of said mouthpiece.

7. The invention of claim 2 wherein said containment baffle is located at an upstream end of said mouthpiece.

8. The invention of claim 1 wherein said containment baffle defines an inhalation opening area located around a periphery thereof.

9. The invention of claim 8 wherein said inhalation opening area comprises a plurality of openings.

10. The invention of claim 9 wherein said openings are arcuate shaped.

11. An aerosol medication delivery apparatus for use with a pressurized metered dose inhaler canister having medication and a propellant contained therein under pressure, where the pressurized metered dose inhaler canister has a discharge orifice from which the medication and the propellant can be discharged forming an aerosol, the apparatus comprising:
 a chamber housing having an input end and an output end and defining an interior space, wherein said input end is adapted to receive a medication discharged from the discharge orifice of a pressurized metered dose inhaler canister into said interior space and said chamber housing having a central axis and a downstream end; and
 a containment baffle located at said downstream end of said chamber housing to partially block said output end, wherein said containment baffle has a curved portion located along and intersecting said central axis of said chamber housing, wherein said curved portion of said containment baffle remains fixed along said central axis relative to said output end of said chamber housing, and wherein said curved portion has a convex surface facing said input end of said chamber housing.

12. The invention of claim 11 further comprising a mouthpiece located at said output end of said chamber housing, wherein said mouthpiece forms said containment baffle.

13. The invention of claim 12 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

14. The invention of claim 12 further comprising a curved shoulder portion transitioning between said chamber housing and said mouthpiece.

15. The invention of claim 14 wherein an inner surface of said curved shoulder is concave.

16. The invention of claim 12 wherein said containment baffle is located at a downstream end of said mouthpiece.

17. The invention of claim 12 wherein said containment baffle is located at an upstream end of said mouthpiece.

18. The invention of claim 11 wherein said containment baffle defines an inhalation opening area located around a periphery thereof.

19. The invention of claim 18 wherein said inhalation opening area comprises a plurality of openings.

20. The invention of claim 19 wherein said openings are arcuate shaped.

21. An aerosol medication delivery apparatus for use with a pressurized metered dose inhaler canister having medication and a propellant contained therein under pressure, where the pressurized metered dose inhaler canister has a discharge orifice from which the medication and the propellant can be discharged forming an aerosol, the apparatus comprising:
 a chamber housing having an input end and an output end and defining an interior space, wherein said input end is adapted to receive a medication discharged from the discharge orifice of a pressurized metered dose inhaler canister into said interior space and said chamber housing having a central axis and a downstream end; and
 a containment baffle located at said downstream end of said chamber housing to partially block said output end, wherein said containment baffle has a curved portion located along and intersecting said central axis of said chamber housing, wherein said curved portion of said containment baffle remains fixed along said central axis relative to said output end of said chamber housing, and wherein said curved portion is domed and includes a concave surface and a convex surface.

22. An aerosol medication delivery apparatus for use with a pressurized metered dose inhaler canister having medication and a propellant contained therein under pressure, where the pressurized metered dose inhaler canister has a discharge orifice from which the medication and the propellant can be discharged forming an aerosol, the apparatus comprising:
 a chamber housing comprising an input end, an output end and a central axis, wherein said chamber housing defines an interior space, wherein said input end is adapted to receive a medication discharged from the discharge orifice of a pressurized metered dose inhaler canister into said interior space;
 a mouthpiece extending from said output end of said chamber housing, said mouthpiece comprising a containment baffle that blocks at least a portion of said output end, wherein said containment baffle has a curved portion located along and intersecting said central axis of said chamber housing, wherein said curved portion of said containment baffle remains fixed along said central axis relative to said output end of said chamber housing, and wherein said curved portion has a concave surface facing said input end of said chamber housing; and
 a curved shoulder portion transitioning between said chamber housing and said mouthpiece, wherein said curved shoulder portion has an interior concave surface.

23. The invention of claim 22 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

24. The invention of claim 22 wherein said containment baffle defines an inhalation opening area located around a periphery thereof.

25. The invention of claim 24 wherein said inhalation opening area comprises a plurality of openings.

26. The invention of claim 25 wherein said oepnings are arcuate shaped.

27. The invention of claim 22 wherein said containment baffle is located at a downstream end of said mouthpiece.

28. The invention of claim 22 wherein said containment baffle is located at an upstream end of said mouthpiece.

29. An aerosol medication delivery apparatus for use with a pressurized metered dose inhaler canister having medication and a propellant contained therein under pressure, where the pressurized metered dose inhaler canister has a discharge orifice from which the medication and the propellant can be discharged forming an aerosol, the apparatus comprising:

a chamber housing comprising an input end, an output end and a central axis, wherein said chamber housing defines an interior space, wherein said input end is adapted to receive a medication discharged from the discharge orifice of a pressurized metered dose inhaler canister into said interior space;

a mouthpiece extending from said output end of said chamber housing, said mouthpiece comprising a containment baffle that blocks at least a portion of said output end, wherein said containment baffle has a curved portion located along and intersecting said central axis of said chamber housing, wherein said curved portion of said containment baffle remains fixed along said central axis relative to said output end of said chamber housing, and wherein said curved portion has a convex surface facing said input end of said chamber housing; and curved shoulder portion transitioning between said chamber housing and said mouthpiece, wherein said curved shoulder portion has an interior concave surface.

30. The invention of claim 29 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

31. The invention of claim 29 wherein said containment baffle defines an inhalation opening area located around a periphery thereof.

32. The invention of claim 31 wherein said inhalation opening area comprises a plurality of openings.

33. The invention of claim 32 wherein said openings are arcuate shaped.

34. The invention of claim 29 wherein said containment baffle is located at a downstream end of said mouthpiece.

35. The invention of claim 29 wherein said containment baffle is located at an upstream end of said mouthpiece.

36. An aerosol medication delivery apparatus for use with a pressurized metered dose inhaler canister having medication and propellant contained therein under pressure, where the pressurized metered dose inhaler canister has a discharge orifice from which the medication and the propellant can be discharged forming an aerosol, the apparatus comprising:

a chamber housing comprising an input end, an output end and a central axis, wherein said chamber housing defines an interior space, wherein said input end is adapted to receive a medication discharged from the discharge orifice of a pressurized metered dose inhaler canister into said inter space;

mouthpiece extending from said output end of said chamber housing, said mouthpiece comprising a containment baffle that blocks at least a portion of said output end, wherein said containment baffle has a curved portion located along and intersecting said central axis of said chamber housing, wherein said curved portion of said containment baffle remains fixed along said central axis relative to said output end of said chamber housing, and wherein said curved portion is domed and includes a concave surface and a convex surface; and.

a curved shoulder portion transitioning between said chamber housing and said mouthpiece, wherein said curved shoulder portion has an interior concave surface.

37. A method for administering medication from a pressurized metered dose inhaler canister having the medication and a propellant contained therein under pressure, where the pressurized metered dose inhaler canister has a discharge orifice from which the medication and the propellant can be discharged forming an aerosol, the method comprising:

providing a chamber housing having an input end and an output end and defining an interior space, wherein said chamber housing has a central axis and a downstream end; a containment baffle located at said downstream end of the chamber housing to partially block said output end, wherein said containment baffle has a curved portion located along and intersecting said central axis of said chamber housing, wherein said curved portion has a concave surface facing said input end of said chamber housing and wherein said curved portion of said containment baffle remains fixed along said central axis relative to said output end of said chamber housing;

discharging said medication into said chamber housing from said pressurized metered dose inhaler canister;

passing said medication through said baffle; and inhaling said medication.

38. The invention of claim 37 further comprising a mouthpiece located at said output end of said chamber housing, wherein mouthpiece forms said containment baffle, and further comprising disposing said mouthpiece in the mouth of a user prior to said inhaling.

39. The invention of claim 38 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

40. The invention of claim 38 wherein said containment baffle is located at a downstream end of said mouthpiece.

41. The invention of claim 37 wherein said containment baffle defines an inhalation opening area located around a periphery thereof, and wherein said inhaling comprises passing said medication through said inhalation opening area.

42. The invention of claim 41 wherein said inhalation opening area comprises a plurality of openings.

43. A method for administering medication from a pressurized metered dose inhaler canister having the medication and a propellant contained therein under pressure, where the pressurized metered dose inhaler canister has a discharge orifice from which the medication and the propellant can be discharged forming an aerosol, the method comprising:

providing a chamber housing having an input end and an output end and defining an interior space, wherein said chamber housing has a central axis and a downstream end; a containment baffle located at said downstream end of the chamber housing to partially block said output end, wherein said containment baffle has a curved portion located along and intersecting said central axis of said chamber housing, wherein said curved portion has a convex surface facing said input end of said chamber housing and wherein said curved portion of said containment baffle remains fixed along said central axis relative to said output end of said chamber housing;

discharging said medication into said chamber housing from said pressurized metered dose inhaler canister;

passing said medication through said baffle; and inhaling said medication.

44. The invention of claim 43 further comprising a mouthpiece located at said output end of said chamber housing, wherein mouthpiece forms said containment baffle, and further comprising disposing said mouthpiece in the mouth of a user prior to said inhaling.

45. The invention of claim 44 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

46. The invention of claim 44 wherein said containment baffle is located at a downstream end of said mouthpiece.

47. The invention of claim 43 wherein said containment baffle defines an inhalation opening area located around a periphery thereof, and wherein said inhaling comprises passing said medication through said inhalation opening area.

48. The invention of claim 47 wherein said inhalation opening area comprises a plurality of openings.

49. A method for administering medication from a pressurized metered dose inhaler canister having the medication and a propellant contained therein under pressure, where the pressurized metered dose inhaler canister has a discharge orifice from which the medication and the propellant can be discharged forming an aerosol, the method comprising:

providing a chamber housing comprising an input end, an output end and a central axis, wherein said chamber housing defines an interior space; a mouthpiece extending from said output end of said chamber housing, wherein said mouthpiece comprising a containment baffle that blocks at least a portion of said output end, wherein said containment baffle has a curved portion located along and intersecting said central axis of said chamber housing, wherein said curved portion has a concave surface facing said input end of said chamber housing and wherein said curved portion of said containment baffle remains fixed along said central axis relative to said output end of said chamber housing; and a curved shoulder portion transitioning between said chamber housing and said mouthpiece, wherein said curved shoulder portion has an interior concave surface;

discharging said medication into said chamber housing from said pressurized metered dose inhaler canister;

disposing said mouthpiece in a mouth of a user;

passing said medication through said baffle; and inhaling said medication.

50. The invention of claim 49 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

51. The invention of claim 49 wherein said containment baffle defines an inhalation opening area located around a periphery thereof, and wherein said inhaling comprises passing said medication through said inhalation opening area.

52. The invention of claim 51 wherein said inhalation opening area comprises a plurality of openings.

53. The invention of claim 52 wherein said openings are arcuate shaped.

54. A method for administering medication from a pressurized metered dose inhaler canister having the medication and a propellant contained therein under pressure, where the pressurized metered dose inhaler canister has a discharge orifice from which the medication and the propellant can be discharged forming an aerosol, the method comprising:

providing a chamber housing comprising an input end, an output end and a central axis, wherein said chamber housing defines an interior space; a mouthpiece extending from said output end of said chamber housing, wherein said mouthpiece comprising a containment baffle that blocks at least a portion of said output end, wherein said containment baffle has a curved portion located along and intersecting said central axis of said chamber housing, wherein said curved portion has a convex surface facing said input end of said chamber housing and wherein said curved portion of said containment baffle remains fixed along said central axis relative to said output end of said chamber housing; and a curved shoulder portion transitioning between said chamber housing and said mouthpiece, wherein said curved shoulder portion has an interior concave surface;

discharging said medication into said chamber housing from said pressurized metered dose inhaler canister;

disposing said mouthpiece in a mouth of a user;

passing said medication through said baffle; and inhaling said medication.

55. The invention of claim 54 wherein said interior space of said chamber housing has a first cross-sectional area perpendicular to said central axis, and wherein said mouthpiece defines an interior space having a second cross-sectional area perpendicular to said central axis, wherein said second cross-sectional area is less than said first cross-sectional area.

56. The invention of claim 54 wherein said containment baffle defines an inhalation opening area located around a periphery thereof, and wherein said inhaling comprises passing said medication through said inhalation opening area.

57. The invention of claim 56 wherein said inhalation opening area comprises a plurality of openings.

58. The invention of claim 57 wherein said openings are arcuate shaped.

* * * * *

UNITED STATES PATENT AND TRADEMARK OFFICE
CERTIFICATE OF CORRECTION

PATENT NO.    : 6,345,617 B1
DATED         : February 12, 2002
INVENTOR(S)   : Dan Engelbreth et al.

It is certified that error appears in the above-identified patent and that said Letters Patent is hereby corrected as shown below:

<u>Column 12,</u>
Line 55, delete "oepnings" and substitute -- openings -- in its place.

<u>Column 13,</u>
Line 61, immediately after "and" (second occurrence) delete "." (period) at the end of the line.

Signed and Sealed this

First Day of October, 2002

*Attest:*

*Attesting Officer*

JAMES E. ROGAN
*Director of the United States Patent and Trademark Office*